United States Patent [19]

Aoki et al.

[11] Patent Number: 4,564,586

[45] Date of Patent: Jan. 14, 1986

[54] SILVER HALIDE COLOR PHOTOGRAPHIC LIGHT-SENSITIVE MATERIAL

[75] Inventors: Kozo Aoki; Michio Ono; Kiyoshi Nakazyo, all of Kanagawa, Japan

[73] Assignee: Fuji Photo Film Co., Ltd., Kanagawa, Japan

[21] Appl. No.: 696,610

[22] Filed: Jan. 30, 1985

[30] Foreign Application Priority Data

Jan. 31, 1984 [JP] Japan .................................. 59-15502

[51] Int. Cl.$^4$ ............................................. G03C 7/26
[52] U.S. Cl. .................................... 430/505; 430/552; 430/553; 430/558
[58] Field of Search ............... 430/558, 384, 385, 505, 430/552, 553

[56] References Cited

U.S. PATENT DOCUMENTS

| | | | |
|---|---|---|---|
| 4,327,173 | 4/1982 | Aoki et al. | 430/558 |
| 4,430,423 | 2/1984 | Aoki et al. | 430/558 |
| 4,524,132 | 6/1985 | Aoki et al. | 430/558 |

*Primary Examiner*—J. Travis Brown
*Attorney, Agent, or Firm*—Sughrue, Mion, Zinn, Macpeak & Seas

[57] ABSTRACT

A silver halide color photographic light-sensitive material comprising a support having coated thereon at least one silver halide emulsion layer, wherein the silver halide color photographic light-sensitive material contains a cyan dye forming coupler represented by the following general formula (I):

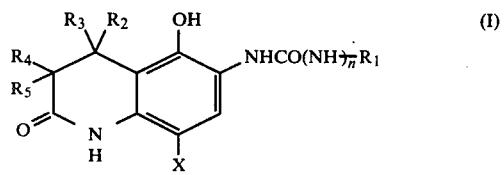

wherein $R_1$ represents a substituted or unsubstituted alkyl group, a substituted or unsubstituted aryl group or a substituted or unsubstituted heterocyclic group; $R_2$, $R_3$, $R_4$ and $R_5$, which may be the same or different, each represents a hydrogen atom, a halogen atom, a substituted or unsubstituted alkyl group, a substituted or unsubstituted alkenyl group, a substituted or unsubstituted aryl group, a substituted or unsubstituted alkoxy group, a substituted or unsubstituted aryloxy group, a substituted or unsubstituted alkylthio group, a substituted or unsubstituted arylthio group, a substituted or unsubstituted acylamino group, a substituted or unsubstituted sulfonamido group, a substituted or unsubstituted alkoxycarbonyl group, a substituted or unsubstituted arylcarbonyl group, a substituted or unsubstituted carbonyl group or a nitrile grout, or $R_2$ and $R_3$ or $R_4$ and $R_5$ may together represents an alkylidene group, $R_2$, $R_3$, $R_4$ and $R_5$ may combine each other to form a ring, three or more of $R_2$, $R_3$, $R_4$ and $R_5$ are not hydrogen atom at the same time and when two of $R_2$, $R_3$, $R_4$ and $R_5$ are hydrogen atoms at the same time, $R_2$, $R_3$, $R_4$ and $R_5$ combine each other to form a ring or $R_2$ and $R_3$ or $R_4$ and $R_5$ are hydrogen atoms; X represents a hydrogen atom or a group capable of being released upon an oxidative coupling with a developing agent; and n represents 0 or 1.

The cyan dye forming coupler can provide a cyan color image having excellent fastness to light and heat and have good solubility in an organic solvent having a high boiling point.

18 Claims, No Drawings

SILVER HALIDE COLOR PHOTOGRAPHIC LIGHT-SENSITIVE MATERIAL

FIELD OF THE INVENTION

The present invention relates to a silver halide color photographic light-sensitive material containing a novel cyan dye forming coupler.

BACKGROUND OF THE INVENTION

When color development is carried out after a silver halide photographic light-sensitive material is exposed to light, an oxidized aromatic primary amine developing agent reacts with a dye forming coupler to form a color image. In this process, color reproduction by a subtractive process is generally utilized. In accordance with this process, dye images of cyan, magenta and yellow, which are complement colors of red, green and blue, respectively, are formed in order to produce images of red, green and blue.

Phenol derivatives or naphthol derivatives are mainly used as cyan color image forming couplers. However, the color images formed from conventionally employed phenol derivatives or naphthol derivatives have some problems with respect to durability. For example, color images formed from the 2 acylaminophenol cyan couplers as described in U.S. Pat. Nos. 2,367,531, 3,369,929, 2,423,730 and 2,801,171 generally have inferior fastness to heat. Color images formed from the 2,5-diacylaminophenol cyan couplers as described in U.S. Pat. Nos. 2,772,162 and 2,895,826 generally have inferior fastness to light, and color images formed from 1-hydroxy-2-naphthamide cyan couplers generally have inferior fastness to both light and heat.

On the other hand, color images formed from 5-hydroxy-2(1H)-quinoline derivative or 5-hydroxy-3,4-dihydro-2(1H)-quinolinone derivative cyan couplers as described in Japanese Patent Application (OPI) Nos. 104333/81 (corresponding to U.S. Pat. No. 4,327,173) and 102936/83 are stated to have good fastness in comparison with other cyan couplers. (The term "OPI" as used herein refers to a "published an unexamined Japanese patent application".) However, these couplers are still insufficient in terms of preservation for a long period of time. Further, these couplers are disadvantageous because they easily crystallize when added to the photographic emulsion, due to their low solubility in an organic solvent having a high boiling point.

SUMMARY OF THE INVENTION

It is an object of the present invention to provide a silver halide color photographic light-sensitive material containing a cyan color image forming coupler wherein the above-described defects are eliminated.

Another object of the present invention is to provide a cyan color image forming coupler wherein above-described defects are eliminated and which can form a color image durable for a long period of time.

A further object of the present invention is to provide a cyan color image forming coupler which has good solubility in an organic solvent having a high boiling point.

Other objects of the present invention will become apparent from the following detailed description and examples.

The above objects of the present invention have been met by a silver halide color photographic light-sensitive material comprising a support having coated thereon at least one silver halide emulsion layer, wherein the silver halide color photographic light-sensitive material contains a cyan dye forming coupler represented by the following general formula (I):

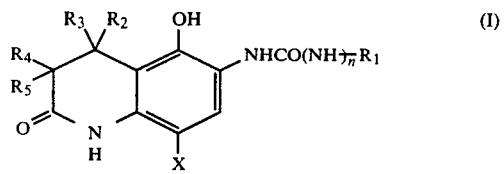

wherein $R_1$ represents a substituted or unsubstituted alkyl group, a substituted or unsubstituted aryl group or a substituted or unsubstituted heterocyclic group; $R_2$, $R_3$, $R_4$ and $R_5$, which may be the same or different, each represents a hydrogen atom, a halogen atom, a substituted or unsubstituted alkyl group, a substituted or unsubstituted alkenyl group, a substituted or unsubstituted aryl group, a substituted or unsubstituted alkoxy group, a substituted or unsubstituted aryloxy group, a substituted or unsubstituted alkylthio group, a substituted or unsubstituted arylthio group, a substituted or unsubstituted acylamino group, a substituted or unsubstituted sulfonamido group, a substituted or unsubstituted alkoxycarbonyl group, a substituted or unsubstituted arylcarbonyl group, a substituted or unsubstituted carbamoyl group or a nitrile grout, or $R_2$ and $R_3$ or $R_4$ and $R_5$ may together represents an alkylidene group, $R_2$, $R_3$, $R_4$ and $R_5$ may combine together to form a ring, three or more of $R_2$, $R_3$, $R_4$ and $R_5$ are not hydrogen atoms at the same time and when two of $R_2$, $R_3$, $R_4$ and $R_5$ are hydrogen atoms at the same time, $R_2$, $R_3$, $R_4$ and $R_5$ combine together to form a ring or $R_2$ and $R_3$ or $R_4$ and $R_5$ are hydrogen atoms; X represents a hydrogen atom or a group capable of being released upon an oxidative coupling with a developing agent; and n represents 0 or 1.

DETAILED DESCRIPTION OF THE INVENTION

Preferred embodiments of $R_1$, $R_2$, $R_3$, $R_4$, $R_5$, X and n in the above general formula (I) will now be described in greater detail below.

In the general formula (I), $R_1$ represents a chain or cyclic alkyl group, preferably an alkyl group having from 1 to 32 carbon atoms (for example, a methyl group, a butyl group, a tridecyl group, a cyclohexyl group, etc.), an aryl group (for example, a phenyl group, a naphthyl group, etc.), or a heterocyclic group (for example, a 2-imidazolyl group, a 2-furyl, a 6-quinolyl group, etc.). These groups can be substituted with one or more substituents selected from an alkyl group, an aryl group, a heterocyclic group, an alkoxy group (for example, a methoxy group, a 2-methoxyethoxy group, etc.); an aryloxy (for example, a phenoxy group, a 2,4-di-tert-amylphenoxy group, a 2-chlorophenoxy group, etc.), a carboxy group, a carbonyl group (for example, an acetyl group, a benzoyl group, etc.), an ester group (for example, a methoxycarbonyl group, a phenoxycarbonyl group, an acetoxy group, a benzoyloxy group, a butoxysulfonyl group, a toluenesulfonyloxy group, etc.), an amido group (for example, an actylamino group, an ethylcarbamoyl group, a dimethylcarbamoyl group, a methanesulfonamido group, a butylsulfamoyl group, etc.), a sulfamido group (for example, a dipropylsulfamoylamino group, etc.), an imido group (for example, a succinimido group, a hydantoinyl group, etc.), a ureido group (for example, a phenylureido group, a dimethylureido group, etc.), a sulfonyl group, (for example, a methanesulfonyl group, etc.), a hydroxy group, a cyano group, a nitro group, a halogen atom and a thio group (for example, an ethylthio group, a phenylthio group, etc.), etc.

In the general formula (I), $R_2$, $R_3$, $R_4$ and $R_5$, which may be the same or different, each represents a hydrogen atom, a halogen atom (for example, a fluorine atom, a chlorine atom, a bromine atom, etc.), a chain or cyclic alkyl group (for example, a methyl group, a butyl group, a dodecyl group, a cyclohexyl group, etc.), an alkenyl group (for example, an allyl group, etc.), an aryl group (for example, a phenyl group, a naphthyl group, etc.), an alkoxy group (for example, a methoxy group, a butoxy group, a tetradecyloxy group, etc.), an aryloxy group (for example, a phenoxy group, etc.), an alkylthio group (for example, a butylthio group, etc.), an arylthio group (for example, a phenylthio group, etc.), an acylamino group (for example, an acetamido group, a benzoylamino group, etc.), a sulfonamido group (for example, a methanesulfonamido group, etc.), an alkoxycarbonyl group (for example, an ethoxycarbonyl group, etc.), an aryloxycarbonyl group (for example, a phenoxycarbonyl group, etc.), a carbamoyl group (for example, a diethylcarbamoyl group, a phenylcarbamoyl group, etc.) or a nitrile group, or $R_2$ and $R_3$ or $R_4$ and $R_5$ may together represents an alkylidene group. Of the groups, the groups which can be substituted may be substituted with one or more substituents as described for $R_1$ above.

In the general formula (I), two of $R_2$, $R_3$, $R_4$ and $R_5$ may combine together to form a ring.

In the general formula (I), three or more of $R_2$, $R_3$, $R_4$ and $R_5$ are not hydrogen atoms at the same time, and when two of $R_2$, $R_3$, $R_4$ and $R_5$ are hydrogen atoms at the same time, two of $R_2$, $R_3$, $R_4$ and $R_5$ combine together to form a ring or $R_2$ and $R_3$ or $R_4$ and $R_5$ are hydrogen atoms.

In the general formula (I), X represents a hydrogen atom, a halogen atom (for example, a fluorine atom, a chlorine atom, a bromine atom, etc.), or other groups capable of being released upon coupling including, for example, an alkoxy group (for example, an ethoxy group, a dodecyloxy group, a methoxyethylcarbamoyl group, a carboxymethoxy group, a methylsulfonylethoxy group, etc.), an aryloxy group (for example, a phenoxy group, a naphthyloxy group, a 4-carboxyphenoxy group, etc.), an acyloxy group (for example, an acetoxy group, a tetradecanoyloxy group, a benzoyloxy group, etc.), a sulfonyloxy group (for example, a methanesulfonyloxy group, a toluenesulfonyloxy group, etc.), an amido group (for example, a dichloroacetylamino group, a heptafluorobutyrylamino group, a methanesulfonylamino group, a toluenesulfonylamino group, etc.), an alkoxycarbonyloxy group (for example, an ethoxycarbonyloxy group, a benzyloxycarbonyloxy group, etc.), an aryloxycarbonyloxy group (for example, a phenoxycarbonyloxy group, etc.), a thio group (for example, a phenylthio group, a tetrazolylthio group, etc.), an amido group (for example, a succinimido group, a hydantoinyl group, etc.), an azo group (for example, a phenylazo group, etc.) and the like. These groups may contain a photographically useful group. The term "photographically useful group" referred to herein means a group having a photographic action such as, for example, those described in U.S. Pat. No. 4,248,962, e.g., development inhibitor residues, dye residues, coupler residues, developing agent residues, bleach accelerator residues, etc.

In the general formula (I), n represents 0 or 1. When n is 0 in the general formula (I), $R_1$ preferably represents a substituted or unsubstituted alkyl group or a substituted or unsubstituted aryl group and more preferably $R_1$ represents a substituted aryl group. When n is 1 in the general formula (I), $R_1$ preferably represents a substituted aryl group, a substituted or unsubstituted heterocyclic group.

In the general formula (I), n is preferably 0.

When $R_2$ to $R_5$ combine together to form a ring in the general formula (I), a preferred number of the members to form the ring is from 3 to 7 and 5 to 6 is most preferred.

The couplers according to the present invention have greatly improved solubility owing to the restricted substituents for $R_2$ to $R_5$ in comparison with the couplers as described in Japanese Patent Application (OPI) No. 104333/81, etc. Also, they exert excellent properties as illustrated in the Examples hereinafter which are remarkable and surprising. Due to the increase in solubility the photographic light-sensitive materials containing the couplers according to the present invention have greatly improved preservability and are advantageous.

Specific examples of the representative couplers according to the present invention will now be set forth below, but the present invention should not be construed as being limited thereto.

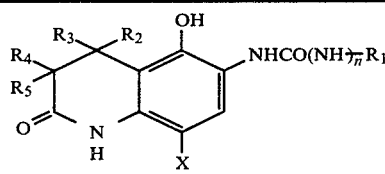

| Coupler No | $R_1$ | $R_2$ | $R_3$ | $R_4$ | $R_5$ | X | n |
|---|---|---|---|---|---|---|---|
| 1 | —CHO—⟨C₄H₉ / C₅H₁₁(t) / C₅H₁₁(t)⟩ | —CH₃ | —CH₃ | —H | —H | —Cl | 0 |
| 2 | —C₇F₁₅ | —CH₃ | —CH₃ | —H | —H | —Cl | 0 |

-continued

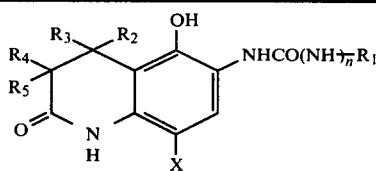

| Coupler No | R₁ | R₂ | R₃ | R₄ | R₅ | X | n |
|---|---|---|---|---|---|---|---|
| 3 | 2-HNSO₂C₁₆H₃₃-phenyl | $-CH_3$ | $-CH_3$ | $-H$ | $-H$ | $-Cl$ | 0 |
| 4 | 4-SO₂C₁₆H₃₃-phenyl | $-CH_3$ | $-CH_3$ | $-H$ | $-H$ | $-H$ | 1 |
| 5 | 3-NHSO₂C₁₆H₃₃-phenyl | $-CH_3$ | $-CH_3$ | $-H$ | $-H$ | $-H$ | 1 |
| 6 | 4-SO₂C₁₂H₂₅-phenyl | $-CH_3$ | $-CH_3$ | $-H$ | $-H$ | $-O(CH_2)_3COOH$ | 1 |
| 7 | 4-CN-phenyl | $-CH_3$ | $-CH_3$ | $-H$ | $-H$ | $-O(CH_2)_2SCHCOOH$ \| $C_{12}H_{25}$ | 1 |
| 8 | 4-SO₂C₁₂H₂₅-phenyl | $-CH_3$ | $-CH_3$ | $-H$ | $-H$ | $-O-C_6H_4-OCH_3$ | 1 |
| 9 | 3-Cl, 4-NHSO₂C₁₂H₂₅-phenyl | $-CH_3$ | $-CH_3$ | $-CH_3$ | $-H$ | $-Cl$ | 0 |
| 10 | $-CH(C_2H_5)O$-[2,4-di-$C_5H_{11}(t)$-phenyl] | $-H$ | $-(CH_2)_4-$ | | $-H$ | $-Cl$ | 0 |
| 11 | 2-HNSO₂C₁₆H₃₃-phenyl | $-(CH_2)_4-$ | | $-H$ | $-H$ | $-Cl$ | 0 |
| 12 | " | $-H$ | $-H$ | $-CONHC_4H_9$ | $-CH_3$ | $-Cl$ | 0 |
| 13 | " | | $=CH_2$ | $-CH_3$ | $-CH_3$ | $-Cl$ | 0 |
| 14 | " | $-CH_3$ | | $-OC_2H_6$ | $-H$ | $-Cl$ | 0 |

-continued

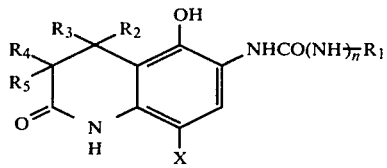

| Coupler No | R₁ | R₂ | R₃ | R₄ | R₅ | X | n |
|---|---|---|---|---|---|---|---|
| 15 | $C_{12}H_{25}$-CHO-C₆H₄-CN | $-CH_3$ | $-CH_3$ | $-CN$ | $-H$ | $-Cl$ | 0 |
| 16 | $-C_3F_7$ | $-C_7H_{15}$ | $-C_2H_5$ | $-H$ | $-H$ | $-Cl$ | 0 |
| 17 | $C_{12}H_{25}$-CHO-C₆H₄-$NHSO_2C_4H_9$ | $-C_2H_5$ | $-C_2H_5$ | $-H$ | $-H$ | $-Cl$ | 0 |
| 18 | $C_{12}H_{25}$-CHO-C₆H₄-$NHSO_2N(CH_3)_2$ | $-C_2H_5$ | $-CH_3$ | $-H$ | $-H$ | $-Cl$ | 0 |
| 19 | -C₆H₄-$COOC_{16}H_{33}$ | $-C_2H_5$ | $-CH_3$ | $-H$ | $-H$ | $-Cl$ | 0 |
| 29 | $C_6H_{13}$-CHO-C₆H₃(Cl)-$tC_5H_{11}$ | $-CH_3$ | $-CH_3$ | $-H$ | $-H$ | $-Cl$ | 0 |

Typical synthesis methods and synthesis examples of the couplers according to the present invention are set forth below.

A 5-hydroxy-3,4-dihydro-2(1H)-quinolinone derivative which is a mother skeleton of the coupler can be synthesized by the methods as described in *Chem. Ind. (London)*, Vol. 1970, page 1435, *Yakugaku Zasshi*, Vol. 96, page 571 (1976), etc. Also, it can be synthesized in accordance with the reaction scheme as described below using 3-amino-4-chlorophenol (Y=OH in the formula A below) or a corresponding compound (for example, Y=Cl in the formula A below, etc.).

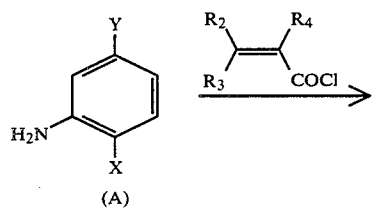

(A)

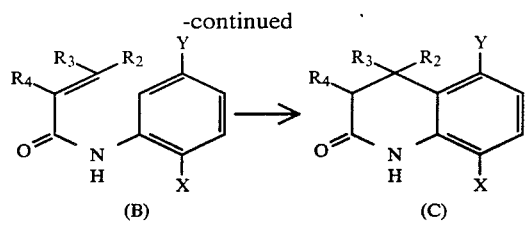

(B) (C)

The corresponding compound (for example, Y=Cl in the formula C above, etc.) can be converted into the desired phenol derivative (Y=OH in the formula C above) by a conventionally known method (for example as described in *Compendium of Organic Synthetic Methods*, page 104, Wiley—Interscience (1971), etc.).

The group capable of being released upon coupling can be introduced into a starting material of the mother skeleton or the mother skeleton synthesized. Then the mother skeleton is subjected to nitration, reduction and reaction with a corresponding acid chloride or carbamic acid ester whereby the coupler is synthesized.

SYNTHESIS EXAMPLE 1

Synthesis of Coupler 3

(i) Synthesis of 5,8-dichloro-4,4-dimethyl-3,4-dihydro-(1H)-quinolinone 38.5 g of 2,5-dichloroaniline was dissolved in a mixture of 150 ml of acetonitrile and 30 ml of pyridine and to the solution was added dropwise 32.5 g of 3,3-dimethylacrylic chloride under cooling with ice. After stirring at 20° C. for 3 hours, the mixture was poured into ice water and the crystals thus-precipitated were collected by filtration and recrystallized from acetonitrile to obtain 44.5 g of the white crystals.

42 g of the crystals thus-obtained were melted by heating at 100° C. on an oil bath to which was added little by little 28 g of anhydrous aluninium chloride. After the completion of the addition, the mixture was stirred for 30 minutes, poured into ice water and extracted with ethyl acetate. The solvent was distilled off under reduced pressure and to the residue was added hexane to solidify. As a result, 32.6 g of 5,8-dichloro-4,4-dimethyl-3,4-dihydro-2(1H)-quinolinone was obtained.

(ii) Synthesis of 8-chloro-5-hydroxy-4,4-dimethyl-6-nitro-3,4-dihydro-2(1H)-quinolinone 32 g of the crystals obtained in Step (i) was dissolved in 160 ml of concentrated surfuric acid and to the solution was added dropwise 1.2 equivalents of nitric acid under cooling with ice. After stirring at 15° C. or below for 3 hours, the mixture was poured into ice water and the crystals thus-precipitated were collected by filtration and recrystallized from acetonitrile to obtain 35.8 g of the light yellow crystals.

34 g of the crystals thus-obtained was dissolved in 150 ml of dimethylacetamide, to the solution was added 60 g of potassium acetate and the mixture was gradually refluxed. After reacting for 10 hours, the mixture was cooled, poured into water and the crystals thus-precipitated were collected by filtration and recrystallized from acetonitrile to obtain 26 g of the desired compound as the yellow crystals.

(iii) Synthesis of Coupler 3

13 g of the crystals obtained in Step (ii) was dissolved in 100 ml of ethanol, to which was added 0.65 g of palladium—carbon catalyst and the mixture was subjected to catalytic reduction in an autoclave. After being absorbed the theoretical amount of hydrogen, the catalyst was removed by filtration and the filtrate was concentrated under reduced pressure to dry state (about 10 g of the crystals). To the residue was added 100 ml of acetonitrile, to the resulting solution was added 19 g of o-hexadecanesulfonamidobenzoyl chloride under refluxing and the mixture was further refluxed for 1 hour. After cooling, ethyl acetate was added to the mixture and washed with water. The solvent was distilled off under reduced pressure to obtain 25 g of the semi-solid substance which was crystallized with a mixture of hexane and ethyl acetate to obtain 18.8 g of the desired Coupler 3.

Melting Point: 99° to 100° C.

Elemental Analysis: Calculated: H: 7.77%; C: 62.99%, N: 6.48%, Found: H: 7.78%, C: 62.82%, N: 6.43%.

SYNTHESIS EXAMPLE 2

Synthesis of Coupler 1

Coupler 1 was obtained in the same manner as described in Step (iii) of Synthesis Example 1 except using 2-(2,4-di-tert-amylphenoxy)hexanoyl chloride in place of the o-hexadecanesulfonamidobenzoyl chloride.

Melting Point: 167° to 169° C.

Elemental Analysis: Calculated: H: 8.29%, C: 69.39%, N: 4.91%, Found: H: 8.27%, C: 69.27%, N: 4.82%.

Other couplers can be synthesized in a manner similar to the above.

The coupler according to the present invention is added to an emulsion layer generally in an amount of from $1\times10^{-3}$ to $7\times10^{-1}$ mol, preferably from $1\times10^{-2}$ to $5\times10^{-1}$ mol per mol of silver.

In order to incorporate the coupler according to the present invention into a silver halide emulsion layer known methods, including those described, e.g., in U.S. Pat. No. 2,322,027 can be used. For example, the coupler can be dissolved into a solvent and then dispersed into a hydrophilic colloid. Examples of solvents usable for this process include organic solvents having a high boiling point, such as alkyl esters of phthalic acid (e.g., dibutyl phthalate, dioctyl phthalate, etc.), phosphates (e.g., diphenyl phosphate, triphenyl phosphate, tricresyl phosphate, dioctyl butyl phosphate, etc.), citrates (e.g., tributyl acetyl citrate, etc.), benzoates (e.g., octyl benzoate, etc.), alkylamides (e.g., diethyl laurylamides, etc.), esters of fatty acids (e.g., dibutoxyethyl succinate, dioctyl azelate, etc.), trimesates (e.g., tributyl trimesate, etc.), phenols (e.g., di-tert-amylphenols, etc.), or the like; and organic solvents having a boiling point of from about 30 to about 150° C., such as lower alkyl acetates (e.g., ethyl acetate, butyl acetate, etc.), ethyl propionate, secondary butyl alcohol, methyl isobutyl ketone, β-ethoxyethyl acetate, methyl cellosolve acetate, or the like. Mixtures of organic solvents having a high boiling point and organic solvents having a low boiling point can also be used.

It is also possible to utilize the dispersing method using polymers, as described in Japanese Patent Publication No. 39853/76 and Japanese Patent Application (OPI) No. 59943/76.

Of the couplers, those having an acid group, such as a carboxylic acid group or a sulfonic acid group, can be introduced into hydrophilic colloids as an aquous alkaline solution.

As the binder or the protective colloid for the photographic emulsion layers or intermediate layers of the photographic light-sensitive material of the present invention, gelatin is advantageously used, but other hydrophilic colloids can be used alone or together with gelatin.

As gelatin in the present invention, not only lime-processed gelatin, but also acid-processed gelatin may be employed. The methods for preparation of gelatin are described in greater detail in Ather Veis, *The Macromolecular Chemistry of Gelatin*, Academic Press (1964).

As the above-described hydrophilic colloids other than gelatin, it is possible to use proteins such as gelatin derivatives, graft polymers of gelatin and other polymers, albumin, casein, etc.; saccharides such as cellulose derivatives such as hydroxyethyl cellulose, carboxymethyl cellulose, cellulose sulfate, etc., sodium alginate, starch derivatives, etc.; and various synthetic hydrophilic high molecular substances such as homopolymers or copolymers, for example, polyvinyl alcohol, polyvinyl alcohol semiacetal, poly-N-vinylpryrrolidone, polyacrylic acid, polymethacrylic acid, polyacrylamide, polyvinyl imidazole, polyvinylvinyl pyrazole, etc.

In the photographic emulsion layer of the photographic light-sensitive material used in the present invention, any of silver bromide, silver iodobromide, silver iodochlorobromide, silver chlorobromide and silver chloride may be used as the silver halide. A preferred silver halide is silver iodobromide containing 15 mol% or less of silver iodide. A silver iodobromide emulsion containing from 2 mol% to 12 mol% of silver iodide is particularly preferred.

Although the mean grain size of silver halide particles in the photographic emulsion (the mean grain size being determined with a grain diameter in those particles which are spherical or nearly spherical, and an edge length in those particles which are cubic as a grain size, and is expressed as a mean value calculated from projected areas) is not particularly limited, it is preferably $3\mu$ or less.

The distribution of grain size may be broad or narrow.

Silver halide particles in the photographic emulsion may have a regular crystal structure, e.g., a cubic or octahedral structure, an irregular crystal structure, e.g., a spherical or plate-like structure, or a composite structure thereof. In addition, silver halide particles composed of those having different crystal structures may be used.

Further, the photographic emulsion wherein at least 50 percent of the total projected area of silver halide particles is super tabular silver halide particles having a diameter at least five times their thickness may be employed.

The inner portion and the surface layer of silver halide particles may be different in phase. Silver halide particles may be those in which a latent image is formed mainly on the surface thereof, or those in which a latent image is formed mainly in the interior thereof.

The photographic emulsion used in the present invention can be prepared in any suitable manner, e.g., by the methods as described in P. Glafkides, *Chimie et Physique Photographique,* Paul Montel (1967), G. F. Duffin, *Photographic Emulsion Chemistry,* The Focal Press (1966), and V. L. Zelikman et al., *Making and Coating Photographic Emulsion,* The Focal Press (1964). That is, any of an acid process, a neutral process, an ammonia process, etc., can be employed.

Soluble silver salts and soluble halogen salts can be reacted by techniques such as a single jet process, a double jet process, and a combination thereof. In addition, there can be employed a method (so-called reversal mixing process) in which silver halide particles are formed in the presence of an excess of silver ions.

As one system of the double jet process, a so-called controlled double jet process in which the pAg in a liquid phase where silver halide is formed is maintained at a predetermined level can be employed. This process can produce a silver halide emulsion in which the crystal form is regular and the grain size is nearly uniform.

Two or more kinds of silver halide emulsions which are prepared separately may be used as a mixture.

The formation or physical ripening of the silver halide particles may be carried out in the presence of cadmium salts, zinc salts, lead salts, thallium salts, iridium salts or its complex salts, rhodium salts or its complex salts, iron salts or its complex salts, and the like.

For removal of soluble salts from the emulsion after precipitate formation or physical ripening, a well known noodle washing process in which gelatin is gelated may be used. In addition, a flocculation process utilizing inorganic salts having a polyvalent anion (e.g., sodium sulfate), anionic surface active agents, anionic polymers (e.g., polystyrenesulfonic acid), or gelatin derivatives (e.g., aliphatic acylated gelatin, aromatic acylated gelatin and aromatic carbamoylated gelatin) may be used.

Silver halide emulsions are usually chemically sensitized. For this chemical sensitization, for example, the methods as described in H. Frieser ed., *Die Grundlagen der Photographischen Prozesse mit Silberhalogeniden,* Akademische Verlagsgesellschaft, pages 675 to 734 (1968) can be used. Namely, a sulfer sensitization process using active gelatin or compounds (e.g., thiosulfates, thioureas, mercapto compounds and rhodanines) containing sulfur capable of reacting with silver; a reduction sensitization process using reducing substances (e.g., stannous salts, amines, hydrazine derivatives, formamidinesulfinic acid, and silane compounds); a noble metal sensitization process using noble metal compounds (e.g., complex salts of Group VIII metals in the Periodic Table, such as Pt, Ir and Pd, etc., as well as gold complex salts); and so forth can be applied alone or in combination with each other.

The photographic emulsion used in the present invention may include various compounds for the purpose of preventing fog formation or of stabilizing photographic performance in the photographic light-sensitive material during the production, storage or photographic processing thereof. For example, those compounds known as antifoggants or stabilizers can be incorporated, including azoles such as benzothiazolium salts, nitroimidazoles, nitrobenzimidazoles, chlorobenzimidazoles, bromobenzimidazoles, mercaptothiazoles, mercaptobenzothiazoles, mercaptobenzimidazoles, mercaptothiadiazoles, aminotrizoles, benzotriazoles, nitrobenzotriazoles, mercaptotetrazoles (particularly 1-phenyl-5-mercaptotetrazole), etc.; mercaptopyrimidines; mercaptotriazines; thioketo compounds such as oxazolinethione, etc.; azaindenes such as triazaindenses, tetraazaindenes (particularly 4-hydroxy-substituted (1,3,3a,7)tetraazaindenes), pentaazaindenes, etc.; benzenethiosulfonic acids; benzenesulfinic acids; benzenesulfonic amides; etc.

In the photographic emulsion layers or other hydrophilic colloid layers of the photographic light-sensitive material of the present invention can be incorporated various surface active agents as coating aids or for other various purposes, e.g. prevention of charging, improvement of slipping properties, acceleration of emulsification and dispersion, prevention of adhesion, and improvement of photographic characteristics (for example, development acceleration, high contrast, and sensitization), etc.

Surface active agents which can be used are nonionic surface active agents, e.g., saponin (steroid-based), alkylene oxide derivatives (e.g., polyethylene glycol, a polyethylene glycol/polypropylene glycol condensate, polyethylene glycol alkyl ethers or polyethylene glycol alkylaryl ethers, polyethylene glycol esters, polyethylene glycol sorbitan esters, polyalkylene glycol alkylamines or polyalkylene glycol alkylamides, and silicone/polyethylene oxide adducts, etc.), glycidol derivatives (e.g., alkenylsuccinic acid polyglyceride and alkylphenol polyglyceride, etc.), fatty acid esters of polyhydric alcohols, and alkyl esters of sugar, etc.; anionic surface active agents containing an acidic group, such as a carboxy group, a sulfo group a phospho group, a sulfuric acid ester group, and a phosphoric acid ester group, for example, alkylcarboxylic acid salts, alkylsulfonic acid salts, alkylbenzenesulfonic acid salts, alkylnaphthalenesulfonic acid salts, alkylsulfuric acid esters, alkylphosphoric acid esters, N-acyl-N-alkyltaurines, sulfosuccinic acid esters, sulfoalkylpolyoxyethylene alkylphenyl ethers, and polyoxyethylene alkylphosphoric acid esters; amphoteric surface active agents, such as amino acids, aminoalkylsulfonic acids, aminoalkylsulfuric acid or aminoalkylphosphoric acid esters, alkylbetains, and amine oxides; and cationic surface active agents, e.g, alkylamine salts, aliphatic or aromatic quaternary ammonium salts, heterocyclic quaternary ammonium salts (e.g., pyridinium and imidazolium), and aliphatic or heterocyclic phosphonium or sulfonium salts.

The photographic emulsion layer of the photographic light-sensitive material of the present invention may contain compounds such as polyalkylene oxide or its ether, ester, amine or like derivatives, thioether compounds, thiomorpholines, quaternary ammonium salt compounds, urethane derivatives, urea derivatives, imidazole derivatives, and 3-pyrazolidones for the purpose of increasing sensitivity or contrast, or of accelerating development.

In the photographic emulsion layer or other hydrophilic colloid layers of the photographic light-sensitive material of the present invention can be incorporated water-insoluble or sparingly soluble synthetic polymer dispersions for the purpose of improving dimensional stability, etc. Synthetic polymers which can be used include homo- or copolymers of alkyl acrylate or methacrylate, alkoxyalkyl acrylate or methacrylate, glycidyl acrylate or methacrylate, acrylamide or methacrylamide, vinyl esters (e.g., vinyl acetate), acrylonitrile, olefins, styrene, etc. and copolymers of the foregoing monomers and acrylic acid, methacrylic acid, $\alpha,\beta$-unsaturated dicarboxylic acid, hydroxyalkyl acrylate or methacrylate, sulfoalkyl acrylate or methacrylate, and styrenesulfonic acid, etc.

In photographic process of layers composed of photographic emulsions in the photographic light-sensitive material of the present invention, any of known procedures and known processing solutions, e.g., those described in *Research Disclosure*, No. 176, pages 28 to 30 can be used. The processing temperature is usually chosen from between 18° C. and 50° C., although it may be lower than 18° C. or higher than 50° C.

Any fixing solutions which have compositions generally used can be used in the present invention. As fixing agents, thiosulfuric acid salts and thiocyanic acid salts, and in addition, organic sulfur compounds which are known effective as fixing agents can be used. These fixing solutions may contain water-soluble aluminum salts as hardeners.

Color developing solutions are usually alkaline aqueous solutions containing color developing agents. As these color developing agents, known primary aromatic amine developing agents, e.g., phenylenediamines such as 4-amino-N,N-diethylaniline, 3-methyl-4-amino-N,N-diethylaniline, 4-amino-N-ethyl-N-$\beta$-hydroxyethylaniline, 3-methyl-4-amino-N-ethyl-N-$\beta$-hydroxyethylaniline, 3-methyl-4-amino-N-ethyl-N-$\beta$-methoxyethylaniline, etc., can be used.

In addition, the compounds as described in L. F. A. Mason, *Photographic Processing Chemistry*, Focal Press, pages 226 to 229 (1966), U.S. Pat. Nos. 2,193,015 and 2,592,364, Japanese Patent Application (OPI) No. 64933/73, etc., may be used.

The color developing solutions can further contain pH buffering agents such as sulfites, carbonates, borates and phosphates of alkali metals, etc. developing inhibitors or anti-fogging agents such as bromides, iodides or organic anti-fogging agents, etc. In addition, if desired, the color developing solution can also contain water softeners; preservatives such as hydroxylamine, etc.; organic solvents such as benzyl alcohol, diethylene glycol, etc.; developing accelerators such as polyethylene glycol, quarternary ammonium salts, amines, etc.; dye forming couplers; competing couplers; fogging agents such as sodium borohydride, etc.; auxiliary developing agents such as 1-phenyl-3-pyrazolidone, etc.; viscosity-imparting agents; polycarbosylic acid type chelating agents; anti-oxidizing agents; and the like.

After color development, the photographic emulsion layer is usually bleached. This bleach processing may be performed simultaneously with a fix processing, or they may be performed independently.

Bleaching agents which can be used include compounds of polyvalent metals, e.g., iron (III), cobalt (III), chromium (VI), and copper (II), peracids, quionones and nitroso compounds. For example, ferricyanides; dichromates; organic complex salts of iron (II) or cobalt (III), e.g., complex salts of aminopolycarboxylic acids (e.g., ethylenediaminetetraacetic acid, nitrilotriacetic acid, 1,3-diamino-2-propanoltetraacetic acid, etc.) or organic acids (e.g., citric acid, tartaric acid, malic acid, etc.); persulfates; permanganates; nitrosophenol, etc. can be used. Of these compounds, potassium ferricyanide, iron (III) sodium ethylenediaminetetraacetate, and iron (III) ammonium ethylenediaminetetraacetate are particularly useful. Ethylenediaminetetraacetic acid iron (III) complex salts are useful in both an independent bleaching solution and a mono-bath bleach-fixing solution.

The photographic emulsion used in the present invention can also be spectrally sensitized with methine dyes or other dyes. Suitable dyes which can be employed include cyanine dyes, merocyanine dyes, complex cyanine dyes, complex merocyanine dyes, holopolar cyanine dyes, hemicyanine dyes, styryl dyes, and hemioxonol dyes. Of these dyes, cyanine dyes, merocyanine dyes and complex merocyanine dyes are particularly useful. Any conventionally utilized nuclei for cyanine dyes are applicable to these dyes as basic heterocyclic nuclei. That is, a pyrroline nucleus, an oxazoline nucleus, a thiazoline nucleus, a pyrrole nucleus, an oxazole nucleus, a thiazole nucleus, a selenazole nucleus, an imidazole nucleus, a tetrazole nucleus, a pyridine nucleus, etc., and further, nuclei formed by condensing alicyclic hydrocarbon rings with these nuclei and nuclei formed by condensing aromatic hydrocarbon rings with these nuclei, that is, an indolenine nucleus, a benzindolenine nucleus, an indole nucleus, abenzoxazole nucleus, anaphthoxazole nucleus, a benzothizole nucleus, anaphthothiazole nuclues, a benzoselenazole nucleus, a benzimidazole nucleus, a quinoline nucleus, etc., are appropriate. The carbon atoms of these nuclei can also be substituted.

The merocyanine dyes and the complex merocyanine dyes that can be employed contain 5- or 6-membered heterocyclic nuclei such as a pyrazolin-5-one nucleus, a thiohydantoin nucleus, a 2-thioxazolidin-2,4-dione nucleus, a thiazolidine-2,4-dione nucleus, a rhodanine nucleus, a thiobarbituric acid nucleus, and the like.

These sensitizing dyes can be employed individually, and can also be employed in combination. A combination of sensitizing dyes is often used particularly for the purpose of supersensitization.

The sensitizing dyes may be present in the emulsion together with dyes which themselves do not give rise to spectrally sensitizing effects but exhibit a supersensitizing effect or materials which do not substantially absorb visible light but exhibit a supersensitizing effect. For example, aminostilbene compounds substituted with a nitrogen-containing heterocyclic ring group (e.g., those described in U.S. Pat. Nos. 2,933,390 and 3,635,721), aromatic organic acid-formaldehyde condensates (e.g., those described in U.S. Pat. No. 3,743,510), cadmium salts, azaindene compounds, and the like, can be present.

The present invention is also applicable to a multilayer multicolor photographic material containing layers sensitive to at least two different spectral wavelength ranges on a support. A multi layer natural color photographic material generally possesses at least one red-sensitive silver halide emulsion layer, at least one green-sensitive silver halide emulsion layer and at least one blue-sensitive silver halide emulsion layer, respectively, on a support. The order of these layers can be varied, if desired. Ordinarily, a cyan forming coupler is present in a red-sensitive emulsion layer, a magenta forming coupler is present in a green-sensitive emulsion layer and a yellow forming coupler is present in a blue-sensitive emulsion layer, respectively. However, if desired, a different combination can be employed.

The photographic emulsion layer of the photographic light-sensitive material of the present invention can be incorporated, in addition to the coupler represented by the general formula (I) described above, with other dye forming couplers, i.e., compounds capable of forming color upon oxidative coupling with aromatic primary amine developing agents (e.g., phenylenediamine derivatives, aminophenol derivatives, etc.) during the course of color development processing. Examples of such couplers include magenta couplers, such as 5-pyrazolone couplers, pyrazolotriazole couplers, pyrazoloimidazole couplers, pyrazolotetrazole couplers, pyrazolopyrazole couplers, pyrazolobenzimidazole couplers, cyanoacetyl-coumarone couplers and open chain acylacetonitrile couplers, etc.; yellow couplers, such as acylacetamide couplers (e.g., benzoylacetanilides, pivaloylacetanilides, etc.), etc.; and cyan couplers, such as naphthol couplers and phenol couplers, etc. It is preferable to use non-diffusible couplers containing a hydrophobic group (so-called ballast group) within the molecule or polymeric couplers. They may be either 4-equivalent or 2-equivalent with respect to silver ions. It is also possible to use colored couplers capable of exerting color correction effects, or couplers capable of releasing development inhibitors during the course of development (so-called DIR couplers).

Further, the emulsion layer may contain non-color-forming DIR coupling compounds which release a development inhibitor, the product of which formed by a coupling reaction is colorless, other than DIR couplers.

Moreover, the photographic light-sensitive material may contain compounds which release a development inhibitor during the course of development, other than DIR couplers.

Two or more kinds of the couplers according to the present invention and the above-described couplers and the like can be incorporated together in the same layer for the purpose of satisfying the properties required to the photographic light-sensitive material, or the same compound can naturally be added to two or more layers.

The photographic light-sensitive material of the present invention may contain inorganic or organic hardeners in the photographic emulsion layer and other hydrophilic colloid layers thereof. For example, chromium salts (e.g., chromium alum, chromium acetate, etc.), aldehydes (e.g., formaldehyde, glyoxal, glutaraldehyde, etc.), N-methylol compounds (e.g., dimethylolurea, methyloldimethylhydantoin, etc.), dioxane derivatives (e.g., 2,3-dihydroxydioxane, etc.), active vinyl compounds (e.g., 1,3,5-triacryloylhexahydro-s-triazine, 1,3-vinylsulfonyl-2-propanol, etc.), active halogen compounds (e.g., 2,4-dichloro-6-hydroxy-s-triazine, etc.), and mucohalogenic acids (e.g., mucochloric acid, mucophenoxychloric acid, etc.) can be used alone or in combination with each other.

In the photographic light-sensitive material of the invention, when dyes, ultraviolet ray absorbing agents, and the like are incorporated in the hydrophilic colloid layers, they may be mordanted with cationic polymers, etc.

The photographic light-sensitive material of the present invention may contain therein hydroquinone derivatives, aminophenol derivatives, gallic acid derivatives, ascorbic acid derivatives, etc., as color fog preventing agents.

The hydrophilic colloid layers of the photographic light-sensitive material of the present invention can contain ultraviolet ray absorbing agents. For example, benzotriazole compounds substituted with aryl groups (e.g., those described in U.S. Pat. No. 3,533,794), 4-thiazolidone compounds (e.g., those described in U.S. Pat. Nos. 3,314,794 and 3,352,681), benzophenone compounds (e.g., those described in Japanese Patent Application (OPI) No. 2784/71), cinnamic acid ester compounds (e.g., those described in U.S. Pat. Nos. 3,705,805 and 3,707,375), butadiene compounds (e.g., those described in U.S. Pat. No. 4,045,229) or benzoxazole compounds (e.g., those described in U.S. Pat. No. 3,700,455) can be employed. Ultraviolet ray absorbing couplers (e.g., α-naphthol type cyan dye forming couplers) and ultraviolet ray absorbing polymers can also be employed. These ultraviolet ray absorbing agents can also be mordanted in a specific layer(s), if desired.

The photographic light-sensitive material of the present invention may contain water-soluble dyes in the hydrophilic colloid layers thereof as filter dye or for various purposes, e.g., irradiation prevention. Examples of such dyes include oxonol dyes, hemioxonol dyes, styryl dyes, merocyanine dyes, cyanine dyes, and azo dyes. In particular, oxonol dyes, hemioxonol dyes, and merocyanine dyes are useful.

In carrying out the present invention, known color fading preventing agents can be used together. Color image stavilizers can be used alone or in combination with each other. Typical known color fading preventing agents include hydroquinone derivatives, gallic acid derivatives, p-alkoxyphenols, p-oxyphenol derivatives, and bisphenols, etc.

The present invention will be explained in greater detail with reference to the following examples, but the present invention should not be construed as being limited thereto.

EXAMPLE 1

A mixture of 10 g of Coupler (1) according to the present invention, 10 g of trioctyl phosphate and 20 ml of ethyl acetate was heated at 50° C. to form a solution. The resulting solution was added to 100 ml of an aqueous solution containing 10 g of gelatin and 0.4 g of sodium dodecylbenzenesulfonate, followed by stirring. The resulting mixture was then finely emulsified and dispersed by passing 5 times through a preheated colloid mill.

The whole emulsion as prepared above was added to 400 g of a photographic emulsion containing 21 g of silver chlorobromide and 24 g of gelatin, and 30 ml of a 2 wt% aqueous solution of 4,6-dichloro-2-hydroxytriazine was added thereto. The resulting mixture was adjusted to a pH of 6.0 and then uniformly coated on a cellulose triacetate film base. The thus-prepared photographic material was designated Sample A.

Samples B, C, and D were prepared in the same manner as described above except that Coupler (1) was replaced by equal molar amounts of Couplers (3), (11) and (15), respectively.

For comparison, Samples E and F were prepared in the same manner as described above, but using equal molar amounts of Comparative Couplers (101) and (102), respectively, in place of Coupler (1).

Comparative Coupler (101)

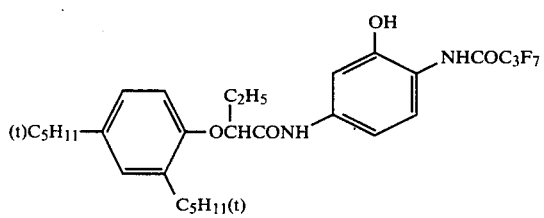

Comparative Coupler (102)

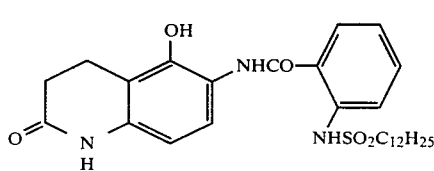

Each film sample thus-obtained was continuously exposed to light through a wedge for sensitometry and then processed as follows:

| Color Development Processing (at 33° C.) | |
| --- | --- |
| Step | Time |
| 1. Color Development | 3 min 30 sec |
| 2. Bleach-Fixing | 1 min 30 sec |
| 3. Washing With Water | 2 min 30 sec |

The processing solution used in each step had the following composition:

| Color Developing Solution | |
| --- | --- |
| Benzyl Alcohol | 15.0 ml |
| Diethylene Glycol | 8.0 ml |
| Ethylenediaminetetraacetic Acid | 5.0 g |
| Sodium Sulfite | 2.0 g |
| Anhydrous Potassium Carbonate | 3.0 g |
| Hydroxylamine Sulfate | 3.0 g |
| Potassium Bromide | 0.6 g |
| 4-Amino-N—ethyl-N—($\beta$-methane-sulfonamidoethyl)-m-toluidine Sesquisulfate Monohydrate | 5.0 g |
| Water to make | 1 liter |
| | (pH 10.2) |
| Bleach-Fixing Solution | |
| Ethylenediaminetetraacetic Acid | 4.0 g |
| Iron (III) Ethylenediamine-tetraacetate | 40 g |
| Sodium Sulfite | 5.0 g |
| Sodium Thiosulfate (70%) | 150 ml |
| Water to make | 1 liter |

Each sample thus-processed was subjected to measurement of the optical density to red light. The results thus-obtained are shown in Table 1 below.

TABLE 1

| Film Sample | Coupler | | Gamma | Maximum Density |
| --- | --- | --- | --- | --- |
| A | (1) | [Present Invention] | 2.70 | 2.91 |
| B | (3) | [Present Invention] | 2.72 | 2.92 |
| C | (11) | [Present Invention] | 2.74 | 2.95 |
| D | (15) | [Present Invention] | 2.68 | 2.91 |
| E | (101) | [Comparison] | 2.52 | 2.80 |
| F | (102) | [Comparison] | 2.23 | 2.36 |

Further, each film thus processed was subjected to testing with respect to fastness. More specifically, the samples were left in a dark place at 100° C. for 6 days, the samples were left in a dark place at 60° C. and 70% RH for 6 weeks, or the samples were irradiated in a xenon test apparatus (100,000 luxes) for 6 days and a density reduction rate of a sample in the area where the initial density was 1.0 was measured to evaluate the fastness. The results thus-obtained are shown in Table 2 below.

TABLE 2

| Film Sample | Coupler | | 100° C. 6 Days | 60° C. 70% RH 6 Weeks | Light (Xenon) 6 Days |
| --- | --- | --- | --- | --- | --- |
| A | (1) | [Present Invention] | 4% | 4% | 11% |
| B | (3) | [Present Invention] | 6% | 5% | 8% |
| C | (11) | [Present Invention] | 6% | 6% | 9% |
| D | (15) | [Present Invention] | 6% | 4% | 12% |
| E | (101) | [Comparison] | 65% | 20% | 41% |
| F | (102) | [Comparison] | 8% | 8% | 20% |

From the results shown above it is apparent that the couplers according to the present invention have the good color forming property and provide the cyan images having excellent fastness to heat and light.

EXAMPLE 2

On a paper support both surfaces of which were laminated with polyethylene were coated a first layer (undermost layer) to a seventh layer (uppermost layer) as shown in Table 3 below in order to prepare a color photographic light-sensitive material which is designated Sample G. In Table 3 below, the coating amounts are set forth in mg/m².

TABLE 3

| Seventh Layer: (Protective layer) | Gelatin (1,000 mg/m²) |
| --- | --- |
| Sixth Layer: (Ultraviolet light-absorbing layer) | Ultraviolet light-absorbing agent*¹ (600 mg/m²) Ultraviolet light-absorbing agent solvent*² |

TABLE 3-continued

| | |
|---|---|
| | (300 mg/m$^2$) |
| | Gelatin (800 mg/m$^2$) |
| Fifth Layer: (Red-sensitive layer) | Silver chlorobromide emulsion (Silver bromide: 50 mol %; silver: 300 mg/m$^2$) Cyan coupler*$^3$ (400 mg/m$^2$) Coupler solvent*$^2$ (400 mg/m$^2$) Gelatin (1,000 mg/m$^2$) |
| Fourth Layer: (Interlayer) | Ultraviolet light-absorbing agent*$^1$ (600 mg/m$^2$) Ultraviolet light-absorbing agent solvent*$^2$ (300 mg/m$^2$) Gelatin (800 mg/m$^2$) |
| Third Layer: (Green-sensitive layer) | Silver chlorobromide emulsion (Silver bromide: 70 mol %; silver: 300 mg/m$^2$) Magenta coupler*$^4$ (200 mg/m$^2$) Coupler solvent*$^5$ (200 mg/m$^2$) Gelatin (1,000 mg/m$^2$) |
| Second Layer: (Interlayer) | Gelatin (1,000 mg/m$^2$) |
| First Layer (Blue-sensitive layer) | Silver chlorobromide emulsion (Silver bromide: 80 mol %; silver: 400 mg/m$^2$) Yellow coupler*$^6$ (300 mg/m$^2$) Coupler solvent*$^7$ (150 mg/m$^2$) Gelatin (1,200 mg/m$^2$) |
| Support: | Paper support both surfaces of which were laminated with polyethylene |

*$^1$Ultraviolet light absorbing agent: 2-(2-Hydroxy-3-sec-butyl-5-tert-butylphenyl)-benzotriazole
*$^2$Solvent: Dibutyl phthalate
*$^3$Coupler: 2-[α-(2,4-Di-tert-pentylphenoxy)-butanamido]-4,6-dichloro-5-methylphenol
*$^4$Coupler: 1-(2,4,6-Trichlorophenyl)-3-(2-chloro-5-tetradecanamido)anilino-2-pyrazolin-5-one
*$^5$Solvent: Tricresyl phosphate
*$^6$Coupler: α-Pivaloyl-α-(2,4-dioxo-5,5-dimethyloxazolidin-3-yl)-2-chloro-5-[α-(2,4-di-tert-pentylphenoxy)butanamido]-acetanilide
*$^7$Solvent: Dioctyl buthyl phosphate Sample H was prepared in the same manner as described for Sample G except using Coupler (3) according to the Present invention in place of the Cyan Coupler (*3).

Each sample was exposed to red light through a continuous wedge and then subjected to the development processing according to the following processing steps.

| Processing Step (at 33° C.) | Time |
|---|---|
| Color Development (A) or (B) | 3 min 30 sec |
| Bleach-Fixing | 1 min 30 sec |
| Washing With Water | 3 min |
| Drying | 10 min |

The processing solution used in each step had the following composition:

| Color Developing Solution (A) | |
|---|---|
| Benzyl Alcohol | 15 ml |
| Diethylene Glycol | 5 ml |
| Potassium Carbonate | 25 g |
| Sodium Chloride | 0.1 g |
| Sodium Bromide | 0.5 g |
| Anhydrous Sodium Sulfite | 2 g |
| Hydroxylamine Sulfate | 2 g |
| N—Ethyl-N—β-methanesulfonamidoethyl-3-methyl-4-aminoaniline Sulfate | 4 g |
| Water to make | 1 liter (adjusting pH 10 with NaOH) |

Color Developing Solution (B)
The same composition as Color Developing Solution (A), except containing no benzyl alcohol.

| Bleach-Fixing Solution | |
|---|---|
| Ammonium Thiosulfate | 124.5 g |
| Sodium Metabisulfite | 13.3 g |
| Anhydrous Sodium Sulfite | 2.7 g |
| Ammonium (Ethylenediaminetetra-acetato)-Iron (III) | 65 g |
| Water to make | 1 liter (adjusting pH 6.8) |

After development-processing, the color density of each sample was measured. The results of fog, gamma, and maximum density (D$_{max}$) measurements with each sample are shown in Table 4 below.

TABLE 4

| Sample | Color Developing Solution (A) | | | Color Developing Solution (B) | | | Remark |
|---|---|---|---|---|---|---|---|
| | Fog | Gamma | D$_{max}$ | Fog | Gamma | D$_{max}$ | |
| G | 0.11 | 2.83 | 2.89 | 0.10 | 2.11 | 2.53 | Comparison |
| H | 0.11 | 2.86 | 3.02 | 0.11 | 2.81 | 2.98 | Present |

It is apparent from the results shown in Table 4 that comparative Sample G has markedly reduced color-forming property in Color Developing Solution (B) containing no benzyl alcohol, whereas Sample H according to the present invention does not undergo substantial reduction in density and gamma and exhibits sufficient color-forming property even in the color developing solution containing no benzyl alcohol.

The reflective absorption spectrum of each of the development-processed samples G and H was measured, and the results thus-obtained are shown in Table 5 below.

TABLE 5

| Sample | Absorption Maximum (nm) | Half Width in Short Wave Side (nm) | Absorption at 420 nm |
|---|---|---|---|
| G | 647 | 86 | 0.390 |
| H | 646 | 82 | 0.252 |

It can be seen from the results shown in Table 5 that the coupler according to the present invention shows narrower half width of absorption, and less subsidiary absorption (in the vicinity of 420 nm), and thus provides favorable hue.

Further, the development-processed samples were subjected to testing with respect to fastness. More specifically, the samples were left in a dark place at 100° C. for 2 days or 4 days, the samples were left in a dark place at 60° C. and 70% RH for 4 weeks and 8 weeks, or the samples were irradiated in a xenon test apparatus (100,000 luxes) for 4 days and 8 days and a density reduction rate of the cyan color image in the area where initial density was 1.0 was measured. The results thus-obtained are shown in Table 6 below.

TABLE 6

| | 100° C. | | 60° C., 70% RH | | Light (Xenon) | |
|---|---|---|---|---|---|---|
| | 2 Days | 4 Days | 4 Weeks | 8 Weeks | 4 Days | 8 Days |
| G [Comparison] | 22% | 48% | 5% | 22% | 4% | 11% |
| H [Present Invention] | 0% | 1% | 0% | 0% | 2% | 6% |

It is apparent from the results shown in Table 6 that the color image formed from the cyan coupler according to the present invention is extremely fast both to light, heat and humidity.

While the invention has been described in detail and with reference to specific embodiments thereof, it will be apparent to one skilled in the art that various changes and modifications can be made therein without departing from the spirit and scope thereof.

What is claimed is:

1. A silver halide photographic light-sensitive material comprising a support having coated thereon at least one silver halide emulsion layer, wherein the silver halide color photographic light-sensitive material contains a cyan dye forming coupler represented by the following general formula (I):

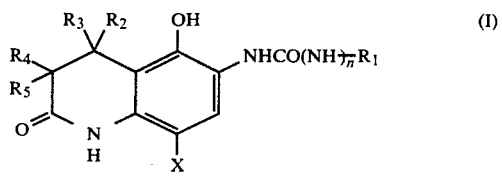

wherein $R_1$ represents a substituted or unsubstituted alkyl group, a substituted or unsubstituted aryl group or a substituted or unsubstituted heterocyclic group; $R_2$, $R_3$, $R_4$ and $R_5$, which may be the same or different, each represents a hydrogen atom, a halogen atom, a substituted or unsubstituted alkyl group, a substituted or unsubstituted alkenyl group, a substituted or unsubstituted aryl group, a substituted or unsubstituted alkoxy group, a substituted or unsubstituted aryloxy group, a substituted or unsubstituted alkylthio group, a substituted or unsubstituted arylthio group, a substituted or unsubstituted acylamino group, a substituted or unsubstituted sulfonamido group, a substituted or unsubstituted alkoxycarbonyl group, a substituted or unsubstituted arylcarbonyl group, a substituted or unsubstituted carbamoyl group or a nitrile group or $R_2$ and $R_3$ or $R_4$ and $R_5$ may together represents an alkylidene group, $R_2$, $R_3$, $R_4$ and $R_5$ may combine together to form a ring, three or more of $R_2$, $R_3$, $R_4$ and $R_5$ are not hydrogen atoms at the same time and when two of $R_2$, $R_3$, $R_4$ and $R_5$ are hydrogen atoms at the same time, $R_2$, $R_3$, $R_4$ and $R_5$ combine together to form a ring or $R_2$ and $R_3$ or $R_4$ and $R_5$ are hydrogen atoms; X represents a hydrogen atom or a group capable of being released upon oxidative coupling with a developing agent; and n represents 0 or 1.

2. A silver halide color photographic light-sensitive material as claimed in claim 1, wherein the alkyl group represented by $R_1$ is an alkyl group having from 1 to 32 carbon atoms.

3. A silver halide color photographic light-sensitive material as claimed in claim 1, wherein the substituent for the alkyl group, the aryl group or the heterocyclic group represented by $R_1$ is selected from an alkyl group, an aryl group, a heterocyclic group, an alkoxy group, an aryloxy group, a carboxy group, a carbonyl group, an ester group, an amido group, a sulfamido group, an imido group, a ureido group, a sulfonyl group, a hydroxy group, a cyano group, a nitro group, a halogen atom and a thio group.

4. A silver halide color photographic light-sensitive material as claimed in claim 1, wherein X represents a hydrogen atom.

5. A silver halide color photographic light-sensitive material as claimed in claim 1, wherein X represents a halogen atom, an alkoxy group, an aryloxy an acyloxy group, a sulfonyloxy group, an amido group, an alkoxycarbonyloxy group, an aryloxycarbonyloxy group, a thio group, an imido group or an azo group.

6. A silver halide photographic light-sensitive material as claimed in claim 1, wherein X represents a photographically useful group.

7. A silver halide color photographic light-sensitive material as claimed in claim 1, wherein $R_1$ represents a substituted or unsubstituted alkyl group or a substituted or unsubstituted aryl group and n represents 0.

8. A silver halide color photographic light-sensitive material as claimed in claim 1, wherein $R_1$ represents a substituted aryl group and n represents 0.

9. A silver halide color photographic light-sensitive material as claimed in claim 1, wherein $R_1$ represents a substituted aryl group or a substituted or unsubstituted heterocyclic group and n represents 1.

10. A silver halide color photographic light-sensitive material as claimed in claim 1, wherein n represents 0.

11. A silver halide color photographic light-sensitive material as claimed in claim 1, wherein the ring formed with $R_2$ to $R^5$ is a 3-membered to 7-membered ring.

12. A silver halide color photographic light-sensitive material as claimed in claim 1, wherein the ring formed with $R_2$ to $R_5$ is a 5-membered or 6-membered ring.

13. A silver halide color photographic light-sensitive material as claimed in claim 1, wherein the cyan dye forming coupler is present in a silver halide emulsion layer.

14. A silver halide color photographic light-sensitive material as claimed in claim 13, wherein the silver halide emulsion layer is a red-sensitive silver halide emulsion layer.

15. A silver halide photographic light-sensitive material as claimed in claim 14, wherein the color photographic material further includes a blue-sensitive silver halide emulsion layer and a green-sensitive silver halide emulsion layer.

16. A silver halide photographic light-sensitive material as claimed in claim 15, wherein the blue-sensitive silver halide emulsion layer contains a yellow color forming coupler and the green-sensitive silver halide emulsion layer contains a magenta color forming coupler.

17. A silver halide photographic light-sensitive material as claimed in claim 1, wherein said coupler is employed in an amount of from $1 \times 10^{-3}$ to $7 \times 10^{-1}$ mole per mole of silver.

18. A silver halide photographic light-sensitive material as claimed in claim 17, wherein said coupler is employed in an amount of from $1 \times 10^{-2}$ to $5 \times 10^{-1}$ mole per mole of silver.

* * * * *